United States Patent
Hupfeld

(10) Patent No.: US 10,080,803 B2
(45) Date of Patent: Sep. 25, 2018

(54) EMULSIFIED KRILL PHOSPHOLIPID COMPOSITIONS

(71) Applicant: Aker BioMarine Antarctic AS, Stamsund (NO)

(72) Inventor: Stefan Hupfeld, Kolbotn (NO)

(73) Assignee: Aker BioMarine Antartic AS, Stamsung (NO)

( * ) Notice: Subject to any disclaimer, the term of this patent is extended or adjusted under 35 U.S.C. 154(b) by 0 days.

(21) Appl. No.: 15/306,352

(22) PCT Filed: Apr. 24, 2015

(86) PCT No.: PCT/EP2015/058984
§ 371 (c)(1),
(2) Date: Oct. 24, 2016

(87) PCT Pub. No.: WO2015/162277
PCT Pub. Date: Oct. 29, 2015

(65) Prior Publication Data
US 2017/0043022 A1    Feb. 16, 2017

(30) Foreign Application Priority Data

Apr. 25, 2014 (GB) .................. 1407345.6

(51) Int. Cl.
| | |
|---|---|
| A61K 47/46 | (2006.01) |
| A61K 47/24 | (2006.01) |
| A61K 47/14 | (2017.01) |
| A61K 9/00 | (2006.01) |
| A61K 9/107 | (2006.01) |

(52) U.S. Cl.
CPC ............ *A61K 47/46* (2013.01); *A61K 9/0019* (2013.01); *A61K 9/1075* (2013.01); *A61K 47/14* (2013.01); *A61K 47/24* (2013.01)

(58) Field of Classification Search
CPC .... A61K 47/46; A61K 9/0019; A61K 9/1075; A61K 47/14; A61K 47/24
USPC ....................................... 514/786
See application file for complete search history.

(56) References Cited

U.S. PATENT DOCUMENTS

| | | |
|---|---|---|
| 2008/0058286 A1 | 3/2008 | Bruheim |
| 2012/0321720 A1 | 12/2012 | Driscoll |
| 2013/0095142 A1 | 4/2013 | Shin |

FOREIGN PATENT DOCUMENTS

| | | |
|---|---|---|
| CN | 102987382 A | 3/2013 |
| EP | 2586449 | 5/2013 |
| WO | 2008/017957 | 2/2008 |
| WO | 2008/117062 | 10/2008 |
| WO | 2009/027692 | 3/2009 |
| WO | 2010/035013 | 4/2010 |
| WO | 2010/097701 | 9/2010 |
| WO | 2011/050474 | 5/2011 |
| WO | 2012/172411 | 12/2012 |
| WO | 2013/102792 | 7/2013 |
| WO | 2013/127727 | 9/2013 |
| WO | 2014/057362 | 4/2014 |
| WO | 2014/207571 | 12/2014 |
| WO | 2015/104401 | 7/2015 |

OTHER PUBLICATIONS

International Search Report, International Patent Application No. PCT/EP2015/058984, dated Jun. 29, 2015.
Batetta B et al. "Endocannabinoids may mediate the ability of (n-3) fatty acids to reduce ectopic fat and inflammatory mediators in obese Zucker rats." (2009) J Nutr 139(8):1495-1501.
Homan R et al. "Rapid separation and quantitation of combined neutral and polar lipid classes by high-performance liquid chromatography and evaporative light-scattering mass detection" (1998) J Chromatogr B Biomed Sci Appl 708:21-26.
Moreau et al. "The analysis of lipids via HPLC with a charged aerosol detector." (2006) Lipids 41:727-734.
Watanabe et al. "Effective Components in Cuttlefish Meal and Raw Krill for Improvement of Quality of Red Seabream Pagrus major Eggs" (1991) Nippon Suisan Gakkaishi 57:681-94.
Winther et al. "Elucidation of Phosphatidylcholine Composition in Krill Oil Extracted from Euphausia superba" (2011) Lipids 46:25-36.

*Primary Examiner* — Kristin Ann Vajda
(74) *Attorney, Agent, or Firm* — Casimir Jones S.C.; J. Mitchell Jones

(57) ABSTRACT

Oil-in-water emulsions are prepared using phospholipids purified from krill.

19 Claims, No Drawings

US 10,080,803 B2

EMULSIFIED KRILL PHOSPHOLIPID COMPOSITIONS

This application is a U.S. 371 national phase entry of International Patent Application No. PCT/EP2015/058984, international filing date Apr. 24, 2015, which claims the benefit of United Kingdom patent application 1407345.6 (filed Apr. 25, 2014), the complete contents of which are hereby incorporated herein by reference for all purposes.

TECHNICAL FIELD

The invention provides oil-in-water emulsions which include krill phospholipids.

BACKGROUND OF THE INVENTION

Oil-in-water emulsions have various uses in the pharmaceutical field. They typically include an aqueous carrier, a biocompatible oil, and a biocompatible surfactant which stabilises the oil droplets.

Reference 1 discloses containers for emulsions, and suggests that the emulsions can include krill oil. Reference 2 discloses pharmaceutical compositions for parenteral administration which comprise krill oil phospholipids in an oil-in-water emulsion, and reports that these emulsions are physically more stable than equivalent emulsions based on egg phospholipids, but it does not report how its emulsions were made. Reference 3 describes further parenteral emulsions which are based on krill phospholipids and include hormones. These emulsions are prepared by dissolving the hormones in an oil, and emulsifying this oil into an aqueous phase together with the krill phospholipids. Reference 4 discloses oil-in-water emulsions which include krill oil as an active ingredient. These emulsions were made by mixing krill oil and soybean oil, and then combining this mixture with an aqueous lecithin solution.

Krill oil is gaining attention as a source of omega-3 fatty acids. Omega-3 fatty acids from natural sources are found predominantly in the form of triglycerides and phospholipids. Phospholipids generally comprise one or two fatty acids groups bound to a phosphate group, usually via a glycerol backbone. The phosphate group is further linked to an organic headgroup, such as a choline or ethanolamine group. In addition to glycerol-derived phospholipids, the term "phospholipid" also encompasses sphingomyelin. Krill oil is distinguished from other sources of omega-3 fatty acids by a high proportion of fatty acids in the form of phospholipids, which may constitute as much as 60% by weight of the oil.

In addition to phospholipids and triglycerides, krill oils also naturally contain astaxanthin, and references 2-4 take advantage of the antioxidant properties of this molecule in order to ensure stability of their emulsions e.g. reference 4 used a krill oil containing 0.095% astaxanthin, and the emulsions in reference 2 included 0.04 g/L astaxanthin. In addition to astaxanthins, the krill oil in reference 4 contains high levels of vitamins A and E (18437.5 IU and 4.2 g per 100 g, respectively). The emulsions also contain oleic acid and/or sodium oleate.

It is an object of the invention to provide further and improved oil-in-water emulsions using phospholipids from krill oil, and methods for their preparation.

DISCLOSURE OF THE INVENTION

The prior art emulsions were prepared from krill oil in which krill phospholipids were present at no more than 60% by weight. The remainder of such krill oils is principally triglycerides, and these will form part of the oil phase in resulting oil-in-water emulsions. By using a krill lipid mixture comprising at least 80% by weight krill phospholipids, the amount of krill triglycerides is reduced, and the inventors have shown that this can provide emulsions having improved physical stability and a lower polydispersity index (PdI). The improved stability is obtained alongside lower zeta-potential than reported for prior art emulsions e.g. as disclosed in reference 3.

The mixing process described on page 39 of reference 3 is flawed because the water/phospholipid mixture which is prepared in step (a) includes a high level of triglycerides. It has now been found that the use of a krill lipid mixture comprising high levels of triglycerides (e.g. greater than 20% by weight) as the krill phospholipid source is not optimal for the formation of emulsions. Without being bound by theory, it is proposed the phospholipids and triglycerides in such krill lipid mixtures may form a thermodynamically-favoured system, thereby reducing the availability of the phospholipids to stabilise an emulsion. By increasing the concentration of phospholipids in the krill lipid mixture, it is believed that their thermodynamic stability is reduced, thereby resulting in emulsions of improved stability.

The invention therefore provides a process for preparing an oil-in-water emulsion, comprising steps of: (a) combining an aqueous carrier and a krill lipid mixture comprising at least 80% by weight of krill phospholipids to provide an aqueous phospholipid mixture; (b) combining the aqueous phospholipid mixture with a metabolisable oil to form the oil-in-water emulsion. It has been found that by combining an aqueous carrier with a krill lipid mixture comprising a high concentration of phospholipids, and therefore a reduced concentration of triglycerides compared to natural krill oil and the prior art discussed above, an improved emulsion is obtained.

The invention further provides an oil-in-water emulsion preparable by a process comprising the above steps (a) and (b).

The invention also provides a process for preparing an oil-in-water emulsion, comprising steps of: (a) combining a metabolisable oil with a krill lipid mixture comprising at least 80% by weight of krill phospholipids to provide an oil-phospholipid mixture; (b) combining the oil-phospholipid mixture with an aqueous carrier to form the oil-in-water emulsion.

The krill lipid mixture is preferably krill oil in which the krill phospholipid content is enriched relative to the natural phospholipid content of krill oil, which is typically in the range of from 20 to 60% by weight of the krill oil. Thus, the non-phospholipid remainder of the krill lipid mixture preferably comprises a major amount of krill triglycerides and minor amounts (if any) of other substances, such as astaxanthin and vitamins A and E.

As discussed above, natural krill oil contains astaxanthin together with vitamins A and E. The presence of high concentrations these substances in pharmaceutical compositions is often undesirable e.g. for pharmacological reasons or due to regulatory issues. Accordingly, the invention aims to minimise the concentrations of these components in the emulsions provided. Thus the invention provides an oil-in-water emulsion comprising a metabolisable oil, an aqueous carrier, and krill phospholipids, wherein the emulsion comprises: (i) less than 400 µg astaxanthin per gram of krill phospholipids; and (ii) less than 10 mg vitamin A per gram of krill phospholipids and/or less than 40 mg vitamin E per gram of krill phospholipids.

Suitably, the concentration of astaxanthin and vitamins A and E in the emulsions of the invention is controlled through the use of a krill lipid mixture comprising at least 80% by weight of krill phospholipids as the phospholipid source, preferably krill oil in which the krill phospholipid content is enriched relative to the natural phospholipid content of krill oil. Enrichment of the krill phospholipids in krill oil may result in a reduction of the weight ratios of astaxanthin, vitamin A and vitamin E in the krill lipid mixture.

Suitably, the oil-in-water emulsion of the invention may be prepared by the method described above.

Krill Lipid Mixtures

Krill is an advantageous source of phospholipids because it is an abundant species which can be harvested easily. Importantly, it is very low in the food chain, which results in a relative lack of pollutants when compared to species that are higher up the food chain. The use of krill oil as a source of phospholipids is also advantageous in view of consumer awareness and distrust of products obtained from genetically-modified organisms.

Emulsions of the invention comprise krill phospholipids. The inventors observed that commercially available krill oils formed poor quality emulsions (e.g. see Example 2). These krill oils include around 45% by weight phospholipids, but the inventors have found that increasing the purity of the krill phospholipids to 80% or more leads to much better emulsion quality e.g. suitable even for pharmaceutical use and parenteral delivery.

Krill lipid mixtures in which 80% or more of the lipid content is krill phospholipids can be prepared in various ways e.g. see references 5-8. In particular, the krill lipid mixture may be obtained by processing krill oil to increase the concentration of krill phospholipids compared to the concentrations found in natural krill oil. Thus emulsions of the invention are made from or comprise a krill lipid mixture comprising at least 80% by weight krill phospholipids (weight krill phospholipids/total weight of krill lipid mixture) e.g. at least 85%, at least 90%, at least 91%, at least 92%, at least 93%, at least 94%, at least 95%, at least 96%, at least 97%, at least 98%, at least 99% or more by weight of krill phospholipids. The invention therefore encompasses the use of highly purified krill phospholipids as the krill lipid mixture.

Provided that 80% or more of the krill lipid mixture is krill phospholipids, it has been found that stable emulsions may be formed even if the krill lipid mixture comprises a minor amount of triglycerides. For example, the krill lipid mixture may comprise from 1% to 20% by weight of triglycerides (weight triglycerides/total weight of krill lipid mixture) e.g. from 2% to 15% by weight, or from 3% to 10% by weight, for example at least 4%, at least 5%, at least 6%, at least 7%, at least 8%, or at least 9% or more by weight of triglycerides. The triglycerides may be derived from the same krill oil source as the krill phospholipids.

The krill lipid mixture comprises less than 400 µg astaxanthin per gram of krill phospholipids, e.g. less than 350 µg, less than 300 µg, less than 250 µg, less than 200 µg, less than 150 µg, less than 100 µg, less than 80 µg, less than 60 µg, less than 50 µg, less than 40 µg, less than 30 µg, less than 20 µg, less than 10 µg, less than 5 µg, less than 2 µg, or less than 1 µg astaxanthin per gram of krill phospholipids.

The krill lipid mixture may optionally comprise at least 0.01 µg astaxanthin per gram of krill phospholipids, e.g. at least 0.1 µg, at least 1 µg, or at least 10 µg astaxanthin per gram of krill phospholipids.

The krill lipid mixture may comprise less than 320 µg astaxanthin per gram of the krill lipid mixture, e.g. less than 300 µg, less than 250 µg, less than 200 µg, less than 150 µg, less than 100 µg, less than 80 µg, less than 60 µg, less than 50 µg, less than 40 µg, less than 30 µg, less than 20 µg, less than 10 µg, less than 5 µg, less than 2 µg, or less than 1 µg astaxanthin per gram of the krill lipid mixture.

The krill lipid mixture may optionally comprise at least 0.01 µg astaxanthin per gram of the krill lipid mixture, e.g. at least 0.1 µg, at least 1 µg, or at least 10 µg astaxanthin per gram of the krill lipid mixture.

The krill lipid mixture may comprise less than 10 mg vitamin A per gram of krill phospholipids, e.g. less than 8 mg, less than 6 mg, less than 4 mg, less than 2 mg, less than 1 mg, less than 500 µg, less than 200 µg, less than 100 µg, less than 50 µg or less than 20 µg vitamin A per gram of krill phospholipids.

The krill lipid mixture may optionally comprise at least 0.1 µg vitamin A per gram of krill phospholipids, e.g. at least 1 µg, or at least 10 µg vitamin A per gram of krill phospholipids.

The krill lipid mixture may comprise less than 8 mg vitamin A per gram of the krill lipid mixture, e.g. less than 6 mg, less than 4 mg, less than 2 mg, less than 1 mg, less than 500 µg, less than 200 µg, less than 100 µg, less than 50 µg or less than 20 µg vitamin A per gram of the krill lipid mixture.

The krill lipid mixture may optionally comprise at least 0.1 µg vitamin A per gram of the krill lipid mixture, e.g. at least 1 µg, or at least 10 µg vitamin A per gram of the krill lipid mixture.

The krill lipid mixture may comprise less than 40 mg vitamin E per gram of krill phospholipids, e.g. less than 35 mg, less than 30 mg, less than 25 mg, less than 20 mg, less than 15 mg, less than 10 mg, less than 5 mg, less than 2 mg, less than 1 mg, less than 500 µg, less than 200 µg, or less than 100 µg vitamin E per gram of krill phospholipids.

The krill lipid mixture may optionally comprise at least 0.1 µg vitamin E per gram of krill phospholipids, e.g. at least 1 µg, or at least 10 µg vitamin E per gram of krill phospholipids.

The krill lipid mixture may comprise less than 32 mg vitamin E per gram of the krill lipid mixture, e.g. less than 30 mg, less than 25 mg, less than 20 mg, less than 15 mg, less than 10 mg, less than 5 mg, less than 2 mg, less than 1 mg, less than 500 µg, less than 200 µg, or less than 100 µg vitamin E per gram of the krill lipid mixture. The krill lipid mixture may optionally comprise at least 0.1 µg vitamin E per gram of the krill lipid mixture, e.g. at least 1 µg, or at least 10 µg vitamin E per gram of the krill lipid mixture.

Alpha-tocopherol may be a useful antioxidant in the krill lipid mixture and in the emulsions prepared from the krill lipid mixture. Alpha-tocopherol may be present in the emulsions of the invention as part of residual vitamin E content of the krill lipid mixture and/or as a separate component. When alpha-tocopherol is used as an antioxidant it is preferably added to the emulsions as a separate component. Preferably, any alpha-tocopherol added to the emulsions is pharmaceutical-grade alpha-tocopherol. Thus, in some embodiments, the process of the invention may comprise the addition of alpha-tocopherol, preferably pharmaceutical-grade alpha-tocopherol, to the emulsion, e.g. in an amount of from 100 µg to 20 mg, 200 µg to 10 mg, or 500 µg to 5 mg per gram of krill phospholipids.

The krill phospholipids used to make the emulsions preferably comprise a mixture of phospholipid compounds of formula (I) as described in detail below.

The krill lipids can be from any suitable species of krill, including Antarctic krill (*Euphausia superba*), Pacific krill (*Euphausia pacifica*) and Northern krill (*Meganyctiphanes norvegica*). In addition to *E. superba*, other species are known to live in the Antarctic, one in genus *Thysanoessa* (*T. macrura*) and six in genus *Euphausia*. These include ice krill (*Euphausia crystallorophias*), *E. frigida, E. longirostris, E. triacantha* and *E. vallentini*. The preferred krill species is *E. superba*.

Aqueous Carriers

Emulsions of the invention include a continuous or bulk aqueous phase. The term "aqueous carrier" refers to a water-containing liquid. The aqueous carrier may be water or an aqueous solution comprising water and one or more soluble excipients, which may be used in order to regulate various properties of the emulsion. The aqueous phase preferably has a pH of 5.5 to 8.5, and may comprise buffers (e.g. phosphate buffer, HEPES, citrate), tonicity regulating agents (such as NaCl, glycerol or mannitol), and stabilising agents (e.g. a chelator such as EDTA, or an anti-oxidant). Examples of appropriate aqueous media include phosphate-buffered saline.

Metabolisable Oils

The present invention is not limited to any particular metabolisable oil compositions. Metabolisable oils as referred to herein may comprise triglycerides, as well as mono- and di-glycerides and free fatty acids. However, references herein to metabolisable oils shall not be taken to include phospholipids. Preferred metabolisable oils comprise at least 90% by weight of triglycerides, e.g. at least 95%, at least 98% or at least 99% by weight of triglycerides.

Preferably, the metabolisable oil is suitable for parenteral administration, e.g. intravenous administration. Examples of suitable metabolisable oils include oils of vegetable and animal origin, particularly vegetable oils and marine oils.

Suitable marine oils comprise fish oils and krill oils. Such oils generally contain triglycerides of fatty acids comprising from 12 to 24 carbon atoms. Fish and krill oils are characterised by a high concentration of polyunsaturated fatty acids and in particular omega-3 fatty acids as triglycerides.

Preferred marine oils comprise omega-3 fatty acids in an amount of at least 40% by weight of the total fatty acid content of the oil (based on the corresponding free fatty acids), e.g. at least 45%, at least 50%, at least 55%, at least 60%, at least 65%, at least 70%, or at least 75% by weight of the total fatty acid content of the oil. Preferably, the oil comprises the omega-3 fatty acids eicosapentaenoic acid (EPA) and docosahexaenoic acid (DHA) in a combined amount of at least 30% by weight of the total fatty acid content of the oil (based on the corresponding free fatty acids), e.g. at least 35%, at least 40%, at least 45%, at least 50%, at least 55%, at least 60% or at least 65% by weight of the total fatty acid content of the oil.

The term "vegetable oil" as used herein refers to oil derived from plant sources, for example seeds and nuts. Vegetable oils generally comprise or consist of triglycerides of fatty acids comprising from 14 to 22 carbon atoms, with varying degrees of unsaturation depending on the plant source. Non-limiting examples of suitable vegetable oils include soybean oil and safflower oil.

The metabolisable oil may further comprise medium chain triglycerides (MCT), which may be synthetic, or derived from natural sources such as vegetable oils. As used herein, the term "medium chain triglycerides" refers to triglycerides derived from fatty acids comprising from 6 to 14 carbon atoms. Preferably, the term "medium chain triglycerides" refers to triglycerides in which at least 50 wt % of the fatty acid residues have from 6 to 14 carbon atoms (based on the corresponding free fatty acids). MCT may suitably be present in an amount of from 1 to 30 wt %, based on the total weight of the metabolisable oil component, e.g. from 2 to 20 wt %, or from 5 to 15 wt %.

Optionally, the metabolisable oil may comprise triglycerides including omega-6 fatty acids and/or omega-9 fatty acids.

Emulsions

The term "emulsion" as used herein refers to a dispersion of two immiscible liquids. Emulsions comprise droplets of one of the immiscible liquids (the dispersed phase) distributed in the other of the immiscible liquids (the continuous phase). In an oil-in-water emulsion, the dispersed phase comprises oil and the continuous phase comprises an aqueous medium. The droplets of the dispersed phase are commonly referred to as particles, and references herein to "particle size" shall be interpreted accordingly.

The emulsions of the invention comprise less than 400 µg astaxanthin per gram of krill phospholipids in the emulsion, e.g. less than 350 µg, less than 300 µg, less than 250 µg, less than 200 µg, less than 150 µg, less than 100 µg, less than 50 µg, less than 20 µg, less than 10 µg, less than 5 µg, less than 2 µg, or less than 1 µg astaxanthin per gram of krill phospholipids in the emulsion.

The emulsions of the invention may optionally comprise at least 0.01 µg astaxanthin per gram of krill phospholipids in the emulsion, e.g. at least 0.1 µg, at least 1 µg, or at least 10 µg astaxanthin per gram of krill phospholipids in the emulsion.

The overall amount of astaxanthin in the emulsions of the invention may suitably be less than 40 mg/L (based on the total volume of the emulsion), e.g. less than 35 mg/L, less than 30 mg/L, less than 25 mg/L, less than 20 mg/L, less than 15 mg/L, less than 10 mg/L, less than 5 mg/L, less than 2 mg/L, less than 1 mg/L, less than 500 µg/L, less than 200 µg/L, less than 100 µg/L, less than 50 µg/L, less than 20 µg/L or less than 10 µg/L.

The overall amount of astaxanthin in the emulsions of the invention may optionally be at least 10 µg/L, at least 100 µg/L, or at least 1 mg/L.

The emulsions of the invention comprise less than 10 mg vitamin A per gram of krill phospholipids and/or less than 40 mg vitamin E per gram of krill phospholipids.

The emulsions of the invention may comprise less than 10 mg vitamin A per gram of krill phospholipids, e.g. less than 8 mg, less than 6 mg, less than 4 mg, less than 2 mg, less than 1 mg, less than 0.5 mg, less than 0.1 mg, less than 2 mg, less than 1 mg, less than 500 µg, less than 200 µg, 100 µg, less than 50 µg or less than 20 µg vitamin A per gram of krill phospholipids.

The emulsions of the invention may optionally comprise at least 0.1 µg vitamin A per gram of krill phospholipids in the emulsion, e.g. at least 1 µg, or at least 10 µg vitamin A per gram of krill phospholipids in the emulsion.

The overall amount of vitamin A in the emulsions of the invention may suitably be less than 1 g/L (based on the total volume of the emulsion), e.g. 800 mg/L, less than 600 mg/L, less than 400 mg/L, less than 200 mg/L, less than 100 mg/L, less than 50 mg/L, less than 20 mg/L, less than 10 mg/L, less than 5 mg/L, less than 2 mg/L, less than 1 mg/L, less than 500 µg/L or less than 20 µg/L.

The overall amount of vitamin A in the emulsions of the invention may optionally be at least 1 µg/L, e.g. at least 10 µg/L, or at least 100 µg/L.

The emulsions of the invention may comprise less than 40 mg vitamin E per gram of krill phospholipids, e.g. less than 35 mg, less than 30 mg, less than 25 mg, less than 20 mg, less than 15 mg, less than 10 mg, less than 5 mg, less than 2 mg, less than 1 mg, less than 500 µg, less than 200 µg, or less than 100 µg vitamin E per gram of krill phospholipids.

The emulsions of the invention may optionally comprise at least 0.1 µg vitamin E per gram of krill phospholipids in the emulsion, e.g. at least 1 µg, or at least 10 µg vitamin E per gram of krill phospholipids in the emulsion.

The overall amount of vitamin E in the emulsions of the invention may suitably be less than 4 mg/L (based on the total volume of the emulsion), e.g. less than 3.5 g/L, less than 3 g/L, less than 2.5 g/L, less than 2 g/L, less than 1.5 g/L, less than 1 g/L, less than 500 mg/L, less than 200 mg/L, less than 100 mg/L, less than 50 mg/L, less than 20 mg/L, less than 10 mg/L, less than 5 mg/L, less than 2 mg/L, or less than 1 mg/L.

The overall amount of vitamin E in the emulsions of the invention may optionally be at least 1 µg/L, e.g. at least 10 µg/L, or at least 100 µg/L.

Optionally, the emulsions of the invention may comprise alpha-tocopherol as an antioxidant, e.g. in an amount of 100 µg to 20 mg, 200 µg to 10 mg, or 500 µg to 5 mg per gram of krill phospholipids. The overall amount of alpha-tocopherol in the emulsions of the invention may suitably be from 1 mg/L to 2 g/L, from 20 mg/L to 1 g/L, or from 50 mg/L to 500 mg/L (based on the total volume of the emulsion).

The amount of krill phospholipids in the emulsions of the invention is suitably in the range of from 0.05 to 100 g/L, e.g. from 0.1 to 75 g/L, from 0.5 to 50 g/L, from 1 to 30 g/L or from 5 to 25 g/L.

The amount of krill phospholipids in the emulsions of the invention may be in the range of from 0.01 to 0.5 g per gram of metabolisable oil in the emulsions, e.g. from 0.05 to 0.4 g, or from 0.1 to 0.3 g per gram of metabolisable oil.

The amount of metabolisable oil in the emulsions of the invention is suitably in the range of from 10 to 300 g/L, e.g. from 20 to 250 g/L, from 50 to 200 g/L, or from 100 to 200 g/L. As noted above, the emulsions of the invention may be prepared from a krill lipid mixture comprising a minor amount, e.g. 1 wt % or more, of triglycerides, such as krill triglycerides. Those triglycerides form part of the oil phase of the emulsions of the invention and are encompassed within the amounts of metabolisable oil recited herein.

The aqueous carrier is present in the emulsions of the invention as required for volumetric balance. The weight ratio of metabolisable oil to water in the emulsions of the invention is suitably in the range of from 30:70 to 1:98, e.g. from 25:75 to 5:95, or from 20:80 to 10:90.

In a preferred embodiment, the present invention provides an oil-in-water emulsion comprising:
(a) 10 to 300 g/L of a metabolisable oil;
(b) 0.05 to 100 g/L of krill phospholipids; and
(c) an aqueous carrier,
wherein the emulsion comprises: (i) less than 400 µg astaxanthin per gram of krill phospholipids; and (ii) less than 10 mg vitamin A per gram of krill phospholipids and/or less than 40 mg vitamin E per gram of krill phospholipids.

In a further preferred embodiment, the present invention provides an oil-in-water emulsion comprising:
(a) 10 to 300 g/L of a metabolisable oil selected from fish oil, krill oil or a mixture thereof;
(b) 0.05 to 100 g/L of krill phospholipids; and
(c) an aqueous carrier,
wherein the emulsion comprises: (i) less than 400 µg astaxanthin per gram of krill phospholipids; and (ii) less than 10 mg vitamin A per gram of krill phospholipids and/or less than 40 mg vitamin E per gram of krill phospholipids.

The emulsions of the invention are preferably suitable for parenteral administration, e.g. intravenous administration. Preferably, the emulsion is iso-tonic and/or iso-osmotic, for example having an osmolality of 220 to 600 mOsm/kg, e.g. 230 to 360 mOsm/kg. Preferably, the emulsion is sterile.

The emulsions of the invention preferably have a pH of 5.5 to 8.5, e.g. 6 to 8. The pH of the emulsions may be adjusted through the use of an appropriate buffer, as known in the art e.g. NaOH. Suitable buffers include phosphate buffer, HEPES and citrate salts.

In addition to the krill phospholipids, the emulsions of the invention may optionally comprise one or more additional emulsifiers selected from the group of lecithins, e.g. soy lecithin, egg lecithin, sphingosine and mixtures thereof. Where the emulsions comprise additional emulsifiers, the total amount of emulsifiers (including the krill phospholipids) is suitably in the range of from 0.05 to 100 g/L, e.g. from 0.1 to 75 g/L, from 0.5 to 50 g/L, from 1 to 30 g/L or from 5 to 25 g/L. Preferably, the krill phospholipids constitute at least 50 wt % of the total amount of emulsifiers, e.g. at least 60 wt %, at least 70 wt %, at least 80 wt %, at least 90 wt %, at least 95 wt %, at least 98 wt % or at least 99 wt % of the total amount of emulsifiers.

The emulsions of the invention preferably contain oil droplets with a particle diameter within the range of 50 to 500 nm. Within this range the diameter can be controlled by the technique which is chosen for preparation of the emulsion e.g. dispersion into an aqueous medium can give large oil particles whose average diameter can be reduced by further treatment e.g. to the range of 50-250 nm, or even to <50 nm by techniques such as ultrasonication (see below). Apparatuses for determining the average particle diameter of droplets in an emulsion, and the size distribution, are commercially available. These typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan). Dynamic light scattering (DLS) is the preferred method by which droplet diameters are determined. The preferred method for defining the droplet diameters in an emulsion of the invention is a Z-average i.e. the intensity-weighted mean hydrodynamic size of the ensemble collection of oil droplets measured by DLS. The Z-average is derived from cumulants analysis of the measured correlation curve, wherein a single particle size (droplet diameter) is assumed and a single exponential fit is applied to the autocorrelation function. The cumulants analysis algorithm does not yield a distribution but, in addition to an intensity-weighted Z-average, gives a polydispersity index. Thus, references herein to a "diameter" should be taken as an intensity-weighted average, and ideally the Z-average.

Polydispersity is a measure of the width of the size distribution of particles, and is conventionally expressed as the polydispersity index (PdI). A polydispersity index of greater than 0.7 indicates that the sample has a very broad size distribution and a reported value of 0 means that size variation is absent, although values smaller than 0.05 are rarely seen, other than with highly monodisperse standards. It is preferred for oil droplets within the emulsions of the invention to be of a relatively uniform size. Thus the oil droplets within an emulsion of the invention preferably have a PdI of less than 0.4 e.g. less than 0.35, less than 0.3, than 0.275, less than 0.25, less than 0.225, less than 0.2, less than 0.175, less than 0.15, less than 0.125, or even less than 0.1.

In general, a larger PdI (e.g. 0.3 or more) can be acceptable when the oil droplets have a larger average diameter (e.g. 250 nm or more), whereas oil droplets having a smaller average diameter (e.g. less than 100 nm) should ideally have a smaller PdI (e.g. 0.2 or less).

A desired PdI can be achieved using an appropriate method of emulsion manufacture. The PdI of oil droplets can be altered by various techniques. For instance, PdI can be a function of energy input upon preparation as the number of homogenisation cycles.

Stability

The emulsions of the invention are stable. Since the emulsions are intended to be suitable for use in pharmaceutical compositions, they should have an appropriate level of stability or shelf-life. Emulsion stability can be determined on the basis of chemical stability (i.e. the resistance of the metabolisable oil and the phospholipids within the emulsion to degradation e.g. oxidative degradation and the formation of lysolipids, partial glycerides and free fatty acids), on the basis of their physical stability (i.e. the resistance of the emulsions to flocculation, creaming, and/or coalescence), and/or on the basis of their biological stability in vivo after administration to a subject.

The emulsions of the invention are preferably chemically stable over a period of at least two weeks. This is determined by detecting degradation products of the metabolisable oil and the phospholipids. The emulsion is considered to be chemically stable if degradation does not exceed 5% of the total amount of metabolisable oil and phospholipids in the emulsion.

The emulsions of the invention are preferably physically stable over a period of at least two weeks. In general it is considered that the presence of unsaturated phospholipids decreases the physical stability of emulsions. Despite containing relatively high levels of polyunsaturated chains, the emulsions prepared from krill phospholipids have been shown to have useful physical stability. This is advantageous since it means that fewer stability inducing additives are required to be used in the emulsion.

The physical stability of emulsions can be tested by any method which determines the size of oil droplets in an emulsion (e.g. DLS as referred to above). An emulsion is regarded as physically stable over the relevant test period if the average diameter of the oil droplets does not deviate by more than ±30%. Preferably the average diameter of the oil droplets does not deviate by more than ±25%, or more preferably ±20%.

Preferably, the emulsions of the invention are suitable for autoclaving, for example by steam sterilisation according to pharmacopeial requirements (e.g. 121° C., 2 bar for at least 15 min).

Surface Charge

Zeta potential is a measure of the magnitude of the electrostatic or charge repulsion or attraction between particles. The zeta potential of an oil-in-water emulsion arises from the fact that the oil particles may carry a surface charge due to the phospholipid content of the emulsion. The charge will depend both on the nature of the phospholipids and the nature of the medium (e.g. pH). Charge may arise for example as a result of the ionization of groups present on the droplet surface. The zeta potential of emulsions reflects the potential for interaction between the oil droplets and thus can provide an indication of the stability of an emulsion.

The emulsions of the invention preferably have a negative zeta potential. The magnitude of this negative zeta potential is ideally at least −5 mV (e.g. at least −6 mV, −7 mV, −8 mV, −9 mV, −10 mV, or within the range of −5 mV to −30 mV, for example within the range of −5 mV to −20 mV), when measured in 10 mM NaCl. This range is useful because stable emulsions can be achieved while using fewer stability-inducing additives.

Zeta potential is measured using standard techniques known in the art, including laser Doppler velocimetry, in which a voltage is applied across a pair of electrodes at either end of a cell containing the emulsion. Charged particles are attracted to the oppositely charged electrode and their velocity is measured and expressed in unit field strength as their electrophoretic mobility.

Preparing Emulsions

Techniques for preparing oil-in-water emulsions are well known in the art. For example, see: Pharmaceutical Emulsions by D. K. Sarker (Wiley, 2013, ISBN 978-0-470-97683-8). As discussed above, the invention provides a process for preparing an oil-in-water emulsion, comprising steps of: (a) combining an aqueous carrier and a krill lipid mixture comprising at least 80% by weight of krill phospholipids to give an aqueous phospholipid mixture; (b) combining the aqueous phospholipid mixture with a metabolisable oil to form the oil-in-water emulsion. Suitable aqueous carriers, krill lipid mixtures and metabolisable oils are discussed above.

In some embodiments, the process of the invention may comprise one or more steps to reduce the particle size of the oil-in-water emulsion, for instance by the use of a high shear mixer, microfluidisation, or ultrasonication.

In some embodiments, the process of the invention does not comprise a step in which sodium oleate is added to the emulsion.

Additional Components of Emulsions of the Invention

Emulsions of the invention include an aqueous phase, oil droplets, and krill phospholipids, but may optionally also include one or more pharmaceutically acceptable additives selected from chelating agents, complexing agents, preservatives, co-surfactants and viscosity modifiers.

The emulsions of the invention can include active ingredients, and this arrangement is one option instead of providing merely "blank" or "empty" emulsions. Examples of active ingredients include, but are not limited to, active pharmaceutical ingredients (APIs), cosmetic ingredients, or nutritional ingredients.

Emulsions of the invention can include one or more API(s), which can be dissolved in either the aqueous carrier or the metabolisable oil prior to formation of the emulsion, or added after the emulsion is prepared. Preferably, the API(s) are selected from hydrophobic APIs which are dissolved within the oil droplets of the emulsion, or attached to the surface of the oil droplets.

In other embodiments, "empty" emulsions are provided e.g. where the emulsions are used as a source of krill phospholipids, rather than as a delivery vehicle for another component.

Pharmaceuticals

The emulsions of the invention can be formulated as a pharmaceutical. Thus the invention provides a process for preparing a pharmaceutical composition, comprising: (i) preparing an emulsion composition as disclosed above; and (ii) formulating it as a pharmaceutical.

The invention also provides a pharmaceutical composition comprising an emulsion of the invention.

The invention also provides an emulsion of the invention for use in medicine. Similarly, it provides the use of an emulsion of the invention in the manufacture of a medicament for use in medicine. Similarly, it provides a method for treating a subject comprising administering to the subject an emulsion of the invention.

Administration

The emulsions of the invention are suitable for administration by any known route of administration. They may be delivered locally or systemically. They may be delivered by a parenteral route (e.g. by injection, such as subcutaneously, intraperitoneally, intravenously or intramuscularly). Other modes of administration include oral, ocular, and pulmonary administration, and also topical administration (usually dermal) which is particularly suitable for cosmetic applications.

Krill Phospholipids of Formula (I)

As mentioned above, the krill phospholipids used to make the emulsions of the invention preferably comprise a mixture of phospholipid compounds of formula (I):

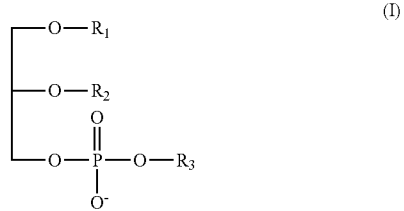

wherein:

$R_1$ and $R_2$ are each independently selected from a fatty acid moiety of formula $-COC_nH_m$, a fatty acid moiety of formula $-CH_2C_nH_m$, and $-H$;

$R_1$ and $R_2$ include omega-3 fatty acid moieties, such that at least 30% by weight of the phospholipid compounds is composed of omega-3 fatty acid moieties;

at least 90% by weight of total omega-3 fatty acid moieties are at position $R_2$;

$R_1$ and $R_2$ are not both H in a phospholipid compound, and $R_1$ or $R_2$ is H in less than 3% by weight of the compounds of formula (I);

$R_3$ is selected from $-H$, a choline moiety, an ethanolamine moiety, a N-acetylethanolamine moiety, an inositol moiety, and a serine moiety; and $R_3$ is a choline moiety in at least 85% by number of the compounds of formula (I).

Typically, and as explained in more detail below, the krill lipid mixtures used to make the emulsions of the invention also have one or more of the following properties:

(a) at least 85% by weight of the krill phospholipids consists of phospholipid compounds of formula (I). In these embodiments, it is preferred that the composition is substantially free from acetone;

(b) the weight ratio of C16:0/C14:0 fatty acid moieties in the krill phospholipids is between 10:1 and 18:1 and/or the weight ratio of C18:4 n–3/C18:3 n–3 fatty acid moieties is between 1:1 and 3:2;

(c) the krill lipid mixture includes less than 300 μg astaxanthins per gram of krill phospholipid;

(d) the krill lipid mixture has less than about 0.03% by weight PUFA polymers (e) the krill phospholipids include both phospholipids where $R_1$ is a fatty acid moiety of formula $-COC_nH_m$ and phospholipids where $R_1$ is a fatty acid moiety of formula $-CH_2C_nH_m$;

(f) the krill phospholipids include both phospholipids where $R_1$ is an omega-3 fatty acid moiety and phospholipids where $R_2$ is an omega-3 fatty acid moiety;

(g) the krill lipid mixture includes less than 5% by weight sphingomyelin; and/or (h) the composition is free from chloroform and hexane.

Mixtures with properties (a), (c), (e), and (h) are preferred. The mixture preferably also has property (b) and/or (g).

$R_1$ and $R_2$ $R_1$ and $R_2$ are each independently selected from the group consisting of a fatty acid moiety of formula $-COC_nH_m$, a fatty acid moiety of formula $-CH_2C_nH_m$, and $-H$. $R_1$ or $R_2$ is $-H$ in only a small fraction of the compounds of formula (I) i.e. less than 3% by weight of the phospholipid compounds are lysophospholipids (see below). Thus most $R_1$ and $R_2$ are $-COC_nH_m$ or $-CH_2C_nH_m$. Where $R_1$ or $R_2$ has formula $-COC_nH_m$ the fatty acid moiety has an ester linkage, but where $R_1$ or $R_2$ has formula $-CH_2CH_m$ the fatty acid moiety has an ether linkage. In these formulae $C_nH_m$ refers to the aliphatic chain which is seen in a naturally-occurring fatty acid (e.g. as seen in krill). For any value of n, m=2n+1 when the fatty acid moiety's aliphatic chain is saturated, but m is reduced by 2 for each unsaturated bond (double bond) in the aliphatic chain i.e. m=2n–1 if one unsaturated bond is present, m=2n–3 if two double bonds are present, m=2n–5 if three double bonds are present, etc. Thus, in general, n is an integer in the range of 4-24 and m=2(n–p)+1, where p is the number of double bonds in the fatty acid moiety. As disclosed in reference 9, the value of n for krill is generally within the range of 11 to 21, and krill phospholipids can include fatty acid moieties with up to six double bonds.

Typically, where a fatty acid moiety at position $R_1$ or $R_2$ is of formula $-CH_2C_nH_m$, the fatty acid moiety is either saturated or monounsaturated. Thus, where $R_1$ or $R_2$ is of formula $-CH_2C_nH_m$, the relationship between n and m is m=2n±1 at that position. In a single molecule, however, it is possible to have a fatty acid moiety of formula $-COC_nH_m$ at one of $R_1$ and $R_2$ (i.e. ester-linked) and a fatty acid of formula $-CH_2C_nH_m$ at the other of $R_1$ and $R_2$ (i.e. ether-linked.). Furthermore, usually 90% (molar) or more of the ether-linked fatty acid moieties will generally be C16 and/or C18 (i.e. where n=15 or 17), unsaturated (e.g. C16:0) or monounsaturated (e.g. C18:1), and ether-linked omega-3 fatty acid moieties are generally not present. Overall, within the mixture, it is preferred that no more than 10% by number of the fatty acid moieties are of formula $-CH_2C_nH_m$ (i.e. 10% or fewer of fatty acid moieties are ether-linked, and more than 90% are ester-linked). It is preferred, though, that the phospholipid mixture should include ether-linked fatty acid moieties i.e. they should not be undetectable. Ether-linked fatty acid moieties are readily detected and quantified by NMR (e.g. see reference 9).

In general, $R_1$ and $R_2$ are not both of formula $-CH_2C_nH_m$ in any single phospholipid molecule. Furthermore, fewer than 5% by number (e.g. fewer than 1% by number, or even zero) of the phospholipid molecules in the mixture have $R_2$ of formula $-CH_2C_nH_m$. In other words, ether-linked fatty acid moieties within the mixture may be seen at $R_1$, but not at $R_2$. Thus, in some embodiments: $R_1$ is selected from a fatty acid moiety of formula $-COC_nH_m$, a fatty acid moiety of formula $-CH_2C_nH_m$, and $-H$; and $R_2$ is selected from a fatty acid moiety of formula $-COC_nH_m$, and $-H$.

In some embodiments: $R_1$ is selected from a fatty acid moiety of formula $-COC_nH_m$, a fatty acid moiety of formula $-CH_2C_nH_m$ where m=2n±1, and $-H$; and $R_2$ is selected from a fatty acid moiety of formula $-COC_nH_m$, and —H. Thus, within the mixture: $R_1$ is an ester-linked fatty acid, an ether-linked saturated or monounsaturated fatty acid, or hydrogen; and $R_2$ is either an ester-linked fatty acid moiety or hydrogen; provided that $R_1$ and $R_2$ are not both hydrogen in a single molecule.

The term "fatty acid" refers to a carboxylic acid with an unbranched aliphatic chain, which may be saturated or unsaturated. These have the general formula $C_nH_m$—COOH. Long chain polyunsaturated fatty acids (LC-PUFAs) are in general fatty acids that have a n value of 19 or more. Polyunsaturated refers to unsaturation at two or more bonds. The term "fatty alcohol" refers to an alcohol with an unbranched aliphatic chain, which may be saturated or unsaturated, and they have the general formula $C_nH_m$—$CH_2OH$. The term "fatty acid moiety" as used herein refers to the aliphatic chain $C_nH_m$ from such fatty acids and fatty alcohols, and the nature of the moiety can be defined by referring to the corresponding fatty acid and/or fatty alcohol. Thus, for a fatty acid moiety of formula —$COC_nH_m$ or —$CH_2C_nH_m$ the corresponding fatty acid is $C_nH_m$—COOH and the corresponding fatty alcohol has formula $C_nH_m$—$CH_2OH$. By way of example the fatty acid DHA ($C_{21}H_{31}$COOH) corresponds to a fatty acid moiety of formula —$COC_{21}H_{31}$ or —$CH_2C_{21}H_{31}$, and EPA ($C_{19}H_{29}$COOH) corresponds to a fatty acid moiety of formula —$COC_{19}H_{29}$ or —$CH_2C_{19}H_{29}$.

$R_1$ and $R_2$ can thus be fatty acid moieties that contain saturated or unsaturated aliphatic chains, but at least 30% by weight of the phospholipid mixture is composed of omega-3 fatty acid moieties at the $R_1$ and $R_2$ positions (i.e. omega-3 fatty acid moieties provide at least 30 g for every 100 g of phospholipid compounds in the mixture). Omega-3 fatty acids are polyunsaturated fatty acids whose final double bond is positioned between the third and fourth carbon atoms from the methyl end of the hydrocarbon chain. Non-limiting examples of omega-3 fatty acids include 5,8,11,14,17-eicosapentaenoic acid (EPA), 4,7,10,13,16,19-docosahexaenoic acid (DHA) and 7,10,13,16,19-docosapentanoic acid (DPA). At least 90% by weight of total omega-3 fatty acid moieties in a phospholipid mixture are at position $R_2$ within formula (I). At least 50% by weight of total omega-3 fatty acid moieties in a phospholipid mixture are EPA and/or DHA (i.e. weight of DHA and EPA/total weight of omega-3 fatty acid moieties in the phospholipids of formula I).

The weight contribution of total omega-3 fatty acid moieties at the $R_1$ and $R_2$ positions can be determined by extracting total phospholipids from the mixture e.g. using the method of reference 10. This is followed by hydrolysis of the lipids to release fatty acids. The released fatty acids are converted to fatty acid esters e.g. fatty acid methyl esters and these esters are analysed e.g. by gas chromatography, HPLC, etc. For instance, the American Oil Chemists' Society has published AOCS Official Method Ce 1b-89 for determining the fatty acid composition of marine oils and marine oil esters by capillary column gas-liquid chromatography. Similarly, reference 9 discloses quantitative analysis of krill oil using HPLC methods based on references 11 and 12 (using evaporative light scattering detection or charged aerosol detection). These established methods provide the amount of specific fatty acids present in a sample, from which the amount of omega-3 fatty acids present in the sample (i.e. in positions $R_1$ and $R_2$ of the phospholipid mixture) can be calculated. In general, references to the content of lipid or phospholipid compositions on a weight/weight basis as referred to herein should be taken as having been determined on the basis of these methods (extraction as in reference 10, followed by processing and analysis by chromatography).

Preferably the krill phospholipids comprise between 30-40% w/w omega-3 fatty acid moieties.

Optionally, the krill phospholipids comprise up to 2% w/w omega-6 fatty acids.

Optionally, the krill phospholipids comprise up to 10% w/w omega-9 fatty acids.

In some embodiments, the phospholipid mixture comprises both EPA and DHA fatty acid moieties, in which case the EPA and DHA moieties are preferably present in a molar ratio of EPA:DHA of from about 1:1 to about 3:1 (e.g. about 1.5:1 to 2:1, or about 1.8:1 to 2.2:1).

Lysophospholipids are formed by hydrolysis of fatty acids from phospholipids, resulting in phospholipids with a single fatty acid moiety. Thus one of $R_1$ or $R_2$ is —H in these lysophospholipid compounds. The invention seeks to avoid high levels of lysophospholipids, and the processes of the invention result in low concentrations of lysophospholipids, namely ≤3% w/w and preferably less than 2%, less than 1%, or even less than 0.5% (weight of lysophospholipid/weight of total phospholipids of formula I). The amount of lysophospholipid may be determined by the HPLC-based analytical methods referred to above, and also by NMR or HP-TLC.

In one embodiment the mixture has a lysophospholipid content of between 1.1-3% w/w, but in other embodiments the mixture has a lysophospholipid content of less than 0.9% w/w.

$R_1$ and $R_2$ are not both H in a phospholipid compound. Furthermore, within the composition, it is preferred that molecules of formula (I) where $R_1$ and $R_2$ are both hydrogen are undetectable.

$R_3$ $R_3$ is H or is selected from a choline, ethanolamine, N-acetylethanolamine, inositol and serine. Choline moieties predominate at $R_3$, and the mixture of phospholipid compounds comprises more than 80% choline moieties at position $R_3$ on a molar % basis (mol of choline moieties/total mol phospholipid compounds of formula I), and preferably more than 85% e.g. at least 86, 87, 88, 89, or 90% choline moieties at position $R_3$ on a molar % basis. The mixture of phospholipid compounds can comprise at least 1% (e.g. about 3-15%, 5-12%, 7-10% or 8-9%) ethanolamine and/or N-acetylethanolamine moieties at position $R_3$ on a molar % basis, and preferably a mixture includes at $R_3$ choline and either or both of ethanolamine and/or N-acetylethanolamine. The mixture of phospholipid compounds can comprise <1% of inositol moieties at position $R_3$ on a molar % basis. These amounts can be determined for example by using NMR. The methods referred to above can also be used to determine the amounts of these components on a w/w basis (in which the amount of each may be expressed in g/100 g oil).

Within the mixture, for molecules where $R_3$ is a choline moiety, it is preferred that around 5-15% by number of these molecules have an ether-linkage at position $R_1$. Thus, where $R_3$ is choline, 5-15% of these molecules have $R_1$ of formula —$CH_2C_nH_m$, where $m=2n±1$.

Within the mixture, for molecules where $R_3$ is an ethanolamine or N-acetylethanolamine moiety, it is preferred that around 35-45% by number of these molecules have an ether-linkage at position $R_1$. Thus, where $R_3$ is ethanolamine or N-acetylethanolamine, 35-45% of these molecules have $R_1$ of formula —$CH_2C_nH_m$, where $m=2n±1$.

Phosphorous-containing groups in phospholipids used with the invention may exist in a number of protonated and deprotonated forms depending on the pH of the surrounding environment, for example the pH of the solvent system in which they are dissolved. Therefore, although a particular form may be illustrated in the formula shown above with a negatively-charged O⁻ group, this is intended to be merely representative and does not limit the invention to a specific protonated or deprotonated form.

Phospholipid Concentration in the Krill Lipid Mixture

In some embodiments at least 85% by weight of the krill lipid mixture consists of phospholipid compounds of formula (I) e.g. at least 90%, at least 95%, at least 96%, at least 97%, at least 98%, or even at least 99%. The low level of impurities means that such compositions are suitable for pharmaceutical use.

These highly pure compositions can be obtained via the use of acetone precipitation, but it is preferred that the compositions are substantially free from residual acetone. Acetone is classified by ICH guideline Q3C as a class 3 solvent i.e. as having low toxic potential. Recommended intake of such solvents is 50 mg per day or less, and so a composition of the invention ideally has an acetone content of less than about 0.5% by weight e.g. less than 0.1%, or less than 0.01%. Acetone removal is very efficient and can achieve levels as low as 20 mg per kg of purified krill phospholipid (i.e. 0.002% by weight or 20 ppm). Alternatively defined, the phospholipids used with the invention can be essentially free from acetone.

Fatty Acid Signature

A phospholipid mixture of the invention can include (a) both C16:0 and C14:0 fatty acid moieties and (b) both C18:4 n−3 and C18:3 n−3 fatty acid moieties.

A phospholipid mixture used with the invention can have: (i) a weight ratio of C16:0/C14:0 fatty acid moieties of between 10:1 and 18:1 e.g. between 12:1 and 16:1; and/or (ii) a weight ratio of C18:4 n−3/C18:3 n−3 fatty acid moieties of between 1:1 and 3:2. Ideally, a mixture has both of these properties.

In some embodiments, a phospholipid mixture of the invention contains <8% oleic acid (molar % of fatty acid moieties which are oleic acid moieties).

Astaxanthins

Contrary to the preference in reference 5, where krill phospholipids include 3 g/kg astaxanthins, phospholipids used with the invention ideally include very low levels of astaxanthins (i.e. free astaxanthin and esters thereof) because the inventors see these compounds as pharmacological impurities despite their advantageous antioxidant properties. The krill lipid mixtures used with the invention can have a concentration of astaxanthins which is less than 400 μg per gram of phospholipid (i.e. less than 0.04% by weight), and preferably less than 100 μg per gram of phospholipid (i.e. less than 0.01% by weight). The krill lipid mixtures used with the invention can even have a concentration of astaxanthins which is less than 20 μg per gram of phospholipid (i.e. less than 0.002% by weight) or less than 20 μg per gram of phospholipid (i.e. less than 0.001% by weight). Astaxanthin content can be measured by HPLC e.g. using UV detection.

Levels of astaxanthins are expressed herein as diol equivalents i.e. as free astaxanthin, without including the weight of any esterification (e.g. to fatty acids).

PUFA Polymers

In some embodiments krill lipid mixtures used with the invention have a low concentration of polymers of polyunsaturated fatty acids. Preferably they have less than about 0.03, less than about 0.02, or less than about 0.01% w/w PUFA polymers. Polymer content is measured e.g. by NMR or gel permeation chromatography.

Sphingomyelins

Sphingomyelins are sphingophospholipids found in animal cell membranes. They are based on sphingosine, which is an 18-carbon amino alcohol with an unsaturated hydrocarbon chain, and they usually consist of phosphocholine and ceramide, or a phosphoethanolamine head group. Reference 6 discloses a krill polar lipid extract obtained using hexane and acetone, including 8% sphingomyelins. Krill phospholipids used with the invention preferably include less than 5% by weight sphingomyelin based on the total amount of phospholipids, and generally include much less than this (or even zero). Thus phospholipids used with the invention may include less than 1% by wt sphingomyelin e.g. less than 0.1%, less than 0.01%, or less than 0.001%, based on the total amount of phospholipids.

Residual Organic Solvents

As mentioned above, when making compositions of the invention it is preferred to use only pharmaceutically acceptable solvent components which are regarded as safe in humans. Pharmaceutically acceptable organic solvents are classified in Q3C 'class 3' (i.e. acetic acid, heptane, acetone, isobutyl acetate, anisole, isopropyl acetate, 1-butanol, methyl acetate, 2-butanol, 3-methyl-1-butanol, butyl acetate, methylethyl ketone, tert-butylmethyl ether, methylisobutyl ketone, cumene, 2-methyl-1-propanol, dimethyl sulfoxide, pentane, ethanol, 1-pentanol, ethyl acetate, 1-propanol, ethyl ether, 2-propanol, ethyl formate, propyl acetate, and formic acid). Thus phospholipids used with the invention are preferably free from organic solvent components which are not in this list e.g. they should be free from chloroform and hexane. If a composition includes a residual organic solvent, this is preferably a 'class 3' solvent, and it is even more preferred that a composition with residual organic solvent should include residues of only 2 or 3 organic solvents in total e.g. residue only of ethanol and acetone.

Omega-6 Fatty Acid Moieties

Omega-6 fatty acids can be inflammatory, so they are ideally kept at low levels in compositions of the invention. Thus in some embodiments of the invention the total amount of omega-6 fatty acids (in particular those contributed by the phospholipid mixture) in an emulsion is less than 2% by weight, and ideally less than 1.5% or even less than 1%.

Free Fatty Acids

In general, emulsions of the invention should include less than 2% by weight free fatty acids, and ideally less than 1%, preferably less than 0.5%. In general, a high level of FFA may indicate a high level of lysophospholipids.

Other Organic Components

Usually, emulsions of the invention are free from canthaxanthin (i.e. free canthaxanthin, and esters thereof, are undetectable). Similarly, they are usually free from flavonoids (i.e. flavonoids are undetectable).

MODES FOR CARRYING OUT THE INVENTION

Example 1

The commercially available krill oil Superba™ may be used as a source of krill phospholipids. The Superba™ oil has a phospholipid concentration of approximately 40-45% w/w, with around 50% w/w neutral lipids (mainly triglycerides). The inventors hypothesised that a purer form of the krill phospholipids might provide emulsions having improved stability.

A frozen paste from krill was subjected to an extraction procedure under a nitrogen atmosphere. The paste comprises about 65% water (assessed via dry matter), 17% lipids (about equal weights of phospholipids and neutral lipids), and about 18% other dry matter, mainly proteins. Within the lipids, the proportions of certain fatty acids by weight were as follows: C16:0 about 15-17%; C14:0 about 6-10%; C18:3 n−3 about 1.4-3.1%; and C18:4 n−3 about 3.5-7%.

100 kg of the frozen coagulum (−20° C.) was added to a vessel. Based on the water content of the coagulum, 350 kg of pure ethanol (99.8% w/w, room temp) was then added to the vessel, giving a final ethanol concentration in the liquid phase of about 84% w/w (~350 kg ethanol in 415 kg liquid solvents).

The mixture was stirred in the vessel for 45 minutes, with gentle heating if required. Four final temperatures were studied in separate batches, namely a) 2° C., b) 10° C., c) 15° C. and d) 20° C. After stirring was complete, the mixtures were allowed to settle, and they each included a red-coloured liquid phase and a wet slurry which contained shell fragments and other insoluble materials. To remove the liquid phase from the slurry the mixtures were decanted, and the liquid material was put through a coarse filter and then serial-filtered through a 75 μm and 5 μm cartridge filter to obtain a) 345 kg, b) 366 kg, c) 372 kg or d) 374 kg of filtrate, with residual material remaining in the filtration cake.

The filtrates were then subjected to a sequence of washes. Firstly, de-ionized water was added to give ~60% w/w ethanol solutions (a: 137 kg water; b: 149 kg; c: 152 kg; d: 155 kg) and the mixtures were stirred for 10-15 minutes and left to settle for 12-24 h at room temperature (15-20° C.) in vessels having a valve at the base. The bottom phase was isolated by draining the bottom phase through the valve, to give between 5.4-9.0 kg of a lipid-rich fraction. The lipid-rich fraction was re-washed 2 to 5 times with 60% w/w ethanol at room temperature to give a final material which contained about 80% by weight phospholipids and 20% neutral lipids.

This lipid-rich material was treated by cold acetone precipitation. Three parts w/w acetone were added and the lipid rich material was dissolved by gentle heating and slow stirring. The stirring was stopped and the mixture was cooled to 4° C. for precipitation. When the precipitation was complete, the upper solvent phase was removed. This cold precipitation procedure was performed three times in total, after first re-dissolving in fresh acetone each time.

The precipitate was then subjected to evaporation and freeze-drying to remove residual acetone and water. Batch c (i.e. extracted at 15° C., then washed 3×60% EtOH before cold acetone precipitation) provided 1.9 kg of solid material (an orange wax) consisting of at least 90% phospholipids. Astaxanthins were present at <2 mg/kg.

Looking at specific fatty acids, proportions were as follows, measured across several batches:

|  | C14:0 | C16:0 | 16/14 Ratio | C18:3 n-3 | C18:4 n-3 | 18:4/18:3 Ratio |
|---|---|---|---|---|---|---|
| Wet paste | 6-10% | 15-17% | 2-2.5 | 1.4-3.1% | 3.5-7% | 2-3 |
| Final material | 1.0-1.5% | 15-17% | 12-16 | 1.0-2.5% | 1.0-2.5% | 1-1.5 |

The purified phospholipids included both ether-linked and ester-linked fatty acids, but 10% or fewer were ether-linked. NMR showed ether-linked fatty acid moieties at position sn1 but not at sn2, and ether-linked fatty acids were either fully saturated or were monounsaturated. Where a phospholipid was a phosphatidylcholine, about 10% of the molecules included ether-linked fatty acids; where a phospholipid was a phosphatidylethanolamine (with or without N-acetylation), about 40% of the molecules included ether-linked fatty acids. PUFAs were seen only with ester linkages. 30-40% by weight of fatty acids in the purified phospholipids were omega-3, and these were distributed at the sn1 and sn2 positions (mainly at sn2). Most of the omega-3 fatty acids were EPA and/or DHA, with about 2× more EPA than DHA.

The lysophosphatidylcholine content (0.2-0.4 mol %) is very low in the purified phospholipids, when compared to the amount in the starting wet material (about 1.2-1.4 mol %). No molecules were seen where fatty acid chains had been lost at both sn1 and sn2 positions. Lyso-phosphatidylethanolamine (with or without N-acetylation) and lyso-phosphatidylinositol also were not seen.

Examples 2 to 4

Three oil-in-water emulsions were prepared using different sources of phospholipids. In example 2 (comparative), the phospholipid source was commercially available krill oil Superba™, containing 45 wt % phospholipids; in example 3 (comparative), the phospholipid source was Egg PC, an essentially pure (>99 wt %) source of phospholipids obtained from egg yolk; and in example 4 (according to the invention), the phospholipid source was the krill lipid mixture prepared in example 1, containing 94 wt % phospholipids and minor amounts of triglycerides and astaxanthin. The other ingredients in the emulsions were MCT, fish oil, glycerol (tonicity regulator), sodium oleate (co-surfactant) and alpha-tocopherol. The total phospholipid (PL) content was adjusted to 1.2% for all emulsions. The amounts of the ingredients in each emulsion are shown in Table 1.

TABLE 1

| Ingredients | Example 2 (Comparative) | Example 3 (Comparative) | Example 4 |
|---|---|---|---|
| PL obtained from Superba (45% PL) | 1.2% | — | — |
| Egg PC | — | 1.2% | — |
| Pure PL 94.4% | — | — | 1.2% |
| Fish oil (EPAX) | 18% | 18% | 18% |
| MCT | 2% | 2% | 2% |
| Glycerol | 2.5% | 2.5% | 2.5% |
| Sodium oleate | 0.03% | 0.03% | 0.03% |
| Alpha-tocopherol | 0.02% | 0.02% | 0.02% |
| Water (Milli-Q ultrapure) | 76.25% | 76.25% | 76.25% |

The ingredients (total ca. 30 mL) were weighed into 50 mL centrifugation tubes and dispersed using an UltraTurrax™ T18 homogeniser at 4000 rpm for 15 min. The tubes were immediately exposed to 5 min ultrasound using a Qsonica™ touch-screen sonicator (70% amplitude, pulse 10 sec, rest 20 sec). The sample temperature did not exceed 40° C. during sonication.

The emulsions were characterized in terms of visible appearance, particle size, particle size distribution, pH, and osmolality, both immediately after preparation and during storage at 5° C. Each emulsion was prepared twice.

Visible Appearance

The 3 different emulsions appeared homogenous after sonication. No visible differences were observed between formulations, except for the more pink color of the Superba-containing emulsions of Example 2 (due to higher levels of astaxanthin). Replicate batches showed the same result.

After one night of storage at 5° C., the emulsions comprising pure-krill PL and egg-PC were still visually homogenous and stable. The emulsions of Example 2 containing Superba were found to be inhomogeneous showing larger oil droplets (coalescence/creaming) on the surface. The phase separation was even more apparent after 2-4 days at 5° C. for the emulsions of Example 2, whereas the emulsions of Examples 3 and 4 remained visually homogenous and stable.

These experiments show that a krill phospholipid mixture comprising 80% or more of krill phospholipids shows an increased capacity to reduce interfacial tension in an emulsion than krill phospholipids in the form of unenriched krill oils (e.g. Superba™). Without being bound by theory, it is believed that the higher content of triglycerides, fatty acids, astaxanthin, vitamins A and E and other minor components of unenriched krill oils may reduce the capacity of the krill phospholipids to stabilise emulsions.

Size

Size and size-distribution were measured after preparation of the emulsions of Examples 3 and 4 using a Malvern Zetasizer particle size analyser (Malvern Instruments). Due to the visible inhomogeneity of the emulsions of Example 2, these were not analyzed. Mean intensity weighted particle diameter and PdI values are given in Table 2.

TABLE 2

| Emulsion | Mean size, nm | PdI |
| --- | --- | --- |
| Example 2 (comparative) | NA | NA |
| Example 3 (comparative) | 635 | 0.576 |
| Example 4 | 452 | 0.536 | pH pH of the emulsions were in the range of 7.8-8.3. No differences in pH between the different formulations were observed. This pH range of krill-containing emulsions is in accordance with previously reported data (See Reference 3).

Osmolality

The osmolality of emulsions was measured by freezing point depression. The osmolality was in the range of 514-552 mOsm/kg. No significant differences were observed between the different formulations. The measured osmolality is in accordance with previous reports for similar emulsions (See Reference 3).

Example 5

Due to the lower concentration of phospholipids in Superba™ krill oil, approximately double the amount is required to obtain equivalent phospholipid concentration compared to the emulsions comprising pure krill PL and egg PC. Accordingly, the emulsions of Example 2 contain approximately 6 wt % more oil in total. To ensure that this slightly higher concentration of oil did not influence on the stability of the emulsions, two more Superba™-containing emulsions were prepared where the excess oil was corrected for by substituting some of the fish oil. However, phase separation was also evident for these batches. Hence, the instability of Superba™-emulsions was not due to higher oil content.

It will be understood that the invention is described above by way of example only and modifications may be made while remaining within the scope and spirit of the invention.

REFERENCES

[1] WO2008/017957.
[2] WO2012/172411.
[3] WO2013/127727.
[4] US-2013/0095142.
[5] WO2011/050474.
[6] Watanabe et al., (1991) *Nippon Suisan Gakkaishi* 57:681-94.
[7] WO2014/207571.
[8] PCT/EP2015/050370.
[9] Winther et al., 2011 *Lipids* 46:25-36.
[10] Bligh & Dyer 1959 *Can. J. Biochem. Physiol.* 37:911-917.
[11] Homan R et al., 1998 *J Chromatogr B Biomed Sci Appl* 708:21-26.
[12] Moreau et al., 2006 *Lipids* 41:727-734.

The invention claimed is:

1. A process for preparing an oil-in-water emulsion, comprising steps of: (a) combining an aqueous carrier and a krill lipid mixture comprising at least 80% by weight of krill phospholipids to provide an aqueous phospholipid mixture; (b) combining the aqueous phospholipid mixture with a metabolizable oil to form the oil-in-water emulsion.

2. The process according to claim 1, wherein the krill lipid mixture: (i) comprises less than 400 μg astaxanthin per gram of krill phospholipids; (ii) comprises less than 10 mg vitamin A per gram of krill phospholipids; or (iii) comprises less than 40 mg vitamin E per gram of krill phospholipids.

3. The process of claim 1, wherein the metabolizable oil comprises at least 90% by weight of triglycerides.

4. The process according to claim 1, wherein the metabolizable oil is selected from the group consisting of vegetable oils, marine oils and mixtures thereof.

5. The process according to claim 4, wherein the marine oil comprises omega-3 fatty acids in an amount of at least 40% by weight of the total fatty acid content of the marine oil.

6. The process according to claim 5, wherein the metabolizable oil comprises eicosapentaenoic acid (EPA) and docosahexaenoic acid (DHA) in a combined amount of at least 30% by weight of the total fatty acid content of the metabolizable oil.

7. The process according to claim 1, further comprising the step of reducing the particle size of the oil-in-water emulsion.

8. An oil-in-water emulsion comprising a metabolizable oil, an aqueous carrier, and krill phospholipids, wherein the emulsion comprises: (i) less than 400 μg astaxanthin per gram of krill phospholipids; and (ii) less than 10 mg vitamin A per gram of krill phospholipids and/or less than 40 mg vitamin E per gram of krill phospholipids.

9. The oil-in-water emulsion according to claim 8, comprising less than 10 mg vitamin A per gram of krill phospholipids and less than 40 mg vitamin E per gram of krill phospholipids.

10. The oil-in-water emulsion according to claim 8, wherein the metabolizable oil is selected from the group consisting of vegetable oils, marine oils and mixtures thereof.

11. The oil-in-water emulsion according to claim 8, comprising less than 40 mg/L astaxanthin and/or less than 1 g/L vitamin A and/or less than 4 mg/L vitamin E.

12. The oil-in-water emulsion according to claim 8, comprising (i) the krill phospholipids in an amount of from 0.05 to 100 g/L; and/or (ii) the metabolizable oil in an amount of from 10 to 300 g/L.

13. The oil-in-water emulsion according to claim 8, wherein the weight ratio of metabolizable oil to water is in the range of from 30:70 to 1:98.

14. The oil-in-water emulsion according to claim 8, wherein the average particle diameter of the oil droplets is in the range of 50 to 500 nm; optionally, wherein the polydispersity index (PdI) of the oil droplets is less than 0.4.

15. The oil-in-water emulsion according to claim 8, wherein the zeta potential of the emulsion is within the range of −5 mV to −30 mV.

16. The oil-in-water emulsion according to claim 8, which is suitable for parenteral administration.

17. The oil-in-water emulsion according to claim 8, further comprising one or more active pharmaceutical ingredients.

18. A process for preparing a pharmaceutical composition, comprising: (i) preparing an oil-in-water emulsion by a process as defined in claim 1; and (ii) formulating the oil-in-water emulsion as a pharmaceutical composition.

19. A pharmaceutical composition comprising an oil-in-water emulsion as defined in claim 1.

* * * * *